US00PP29520P3

(12) United States Plant Patent
Van Swieten

(10) Patent No.: US PP29,520 P3
(45) Date of Patent: Jul. 17, 2018

(54) ***PHALAENOPSIS* ORCHID PLANT NAMED 'PHALDRAWEQ'**

(50) Latin Name: ***Phalaenopsis* hybrid**
Varietal Denomination: PHALDRAWEQ

(71) Applicant: ANTHURA B.V., Bleiswijk (NL)

(72) Inventor: Martinus Nicolaas Gerardus Van Swieten, Utrecht (NL)

(73) Assignee: ANTHURA B.V., Bleiswijk (NL)

( * ) Notice: Subject to any disclaimer, the term of this patent is extended or adjusted under 35 U.S.C. 154(b) by 30 days.

(21) Appl. No.: 15/330,862

(22) Filed: Nov. 8, 2016

(65) Prior Publication Data

US 2018/0132408 P1 May 10, 2018

(51) Int. Cl.
*A01H 5/02* (2018.01)

(52) U.S. Cl.
USPC ..... Plt./311
CPC ..... *A01H 5/02* (2013.01)

(58) Field of Classification Search
USPC ..... Plt./311
See application file for complete search history.

*Primary Examiner* — Keith O Robinson
(74) *Attorney, Agent, or Firm* — Jondle & Associates, P.C.

(57) ABSTRACT

A new and distinct variety of *Phalaenopsis* plant named 'PHALDRAWEQ', particularly characterized by having small, edged purple flowers, 1 to 3 peduncles that are medium long and sturdy, leaves that are oblong, and is propagated by meristem tissue culture, is disclosed.

3 Drawing Sheets

Genus and species: *Phalaenopsis* hybrid.
Variety denomination: 'PHALDRAWEQ'.

BACKGROUND OF THE NEW PLANT

The present invention relates to a new and distinct cultivar of *Phalaenopsis* plant, botanically known as *Phalaenopsis* hybrid of the Orchidaceae family, commonly referred to as moth orchid, and hereinafter referred to by the variety name 'PHALDRAWEQ'.

The new *Phalaenopsis* plant is a product of a planned breeding program conducted by the inventor in Bleiswijk, The Netherlands. The objective of this breeding program was to create a new *Phalaenopsis* plant with many branches and small, edged purple flowers suitable for potted plant production.

The new *Phalaenopsis* plant 'PHALDRAWEQ' is a result of cross-pollination made by the inventor in May 2005 in Bleiswijk, The Netherlands of the proprietary female, or seed parent, *Phalaenopsis* hybrid 'unknown' with the proprietary male, or pollen parent, *Phalaenopsis* hybrid 'unknown'.

The new *Phalaenopsis* was selected by the inventor as a single plant within the progeny of the stated cross-pollination in a controlled greenhouse in Bleiswijk, The Netherlands in May 2008. Asexual reproduction of the new *Phalaenopsis* plant by meristem tissue culture since 2011 in Bleiswijk, The Netherlands, has demonstrated that the new variety reproduces true to type with all of the characteristics, as herein described, firmly fixed and retained through successive generations.

Plant Breeder's Rights for this variety have been applied for in Europe on Apr. 18, 2016. 'PHALDRAWEQ' has not been made publicly available or sold anywhere in the world more than one year prior to the filing date of this application.

SUMMARY OF THE INVENTION

The following are the most outstanding and distinguishing characteristics of this new cultivar when grown under normal horticultural practices in Bleiswijk, The Netherlands and can be used to distinguish 'PHALDRAWEQ' as a new and distinct variety of *Phalaenopsis* plant.

1) Small, edged purple flowers;
2) 1 to 3 peduncles;
3) Peduncle is medium long and sturdy; and
4) Shape of the leaf is oblong.

DESCRIPTION OF THE PHOTOGRAPHS

This new *Phalaenopsis* plant is illustrated by the accompanying photographs which show the overall plant habit including blooms, buds and foliage of the plant; the colors shown are as true as can be reasonably obtained by conventional photographic procedures. The photographs were taken in a greenhouse in Bleiswijk, The Netherlands, from 50-week old plants in September 2016. Colors in the photographs may differ from the color values cited in the detailed botanical description, which accurately describe the actual colors of the new variety.

DESCRIPTION OF THE NEW VARIETY

Figure 1:
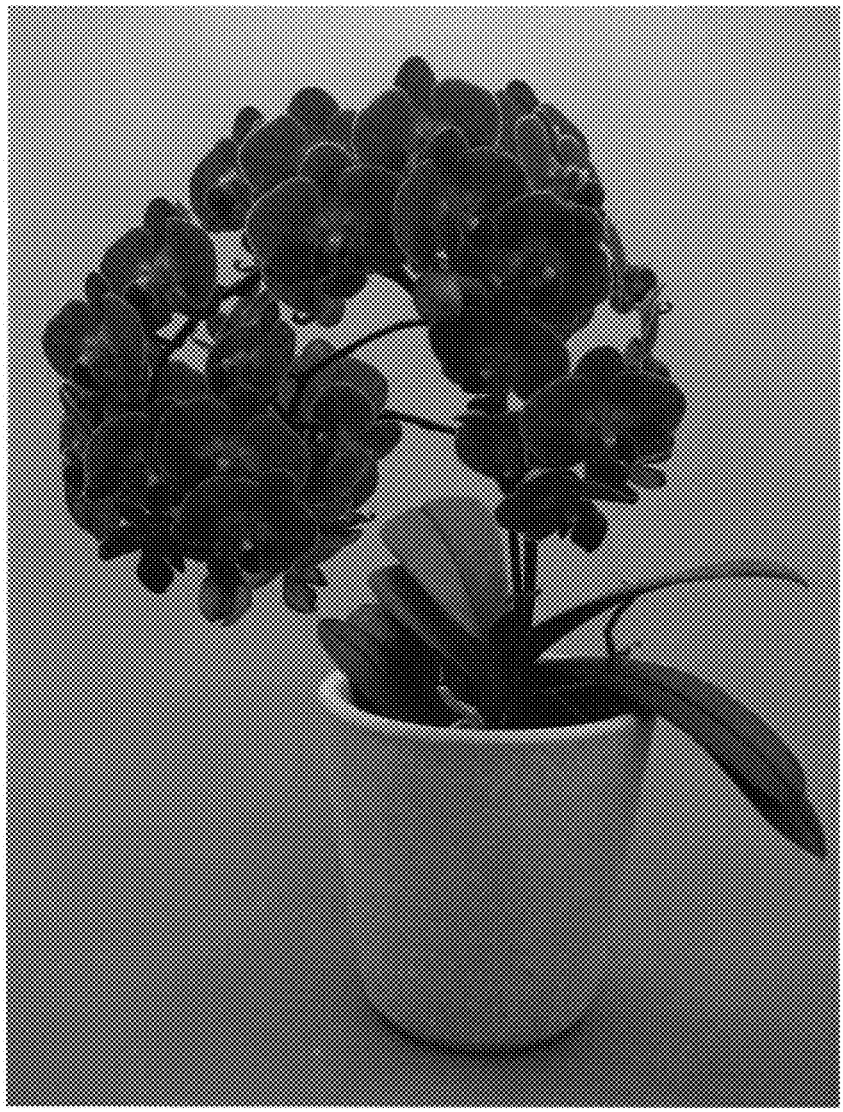
FIG. 1 shows the overall plant habit, including blooms, buds and foliage of 'PHALDRAWEQ'.
Figure 2:
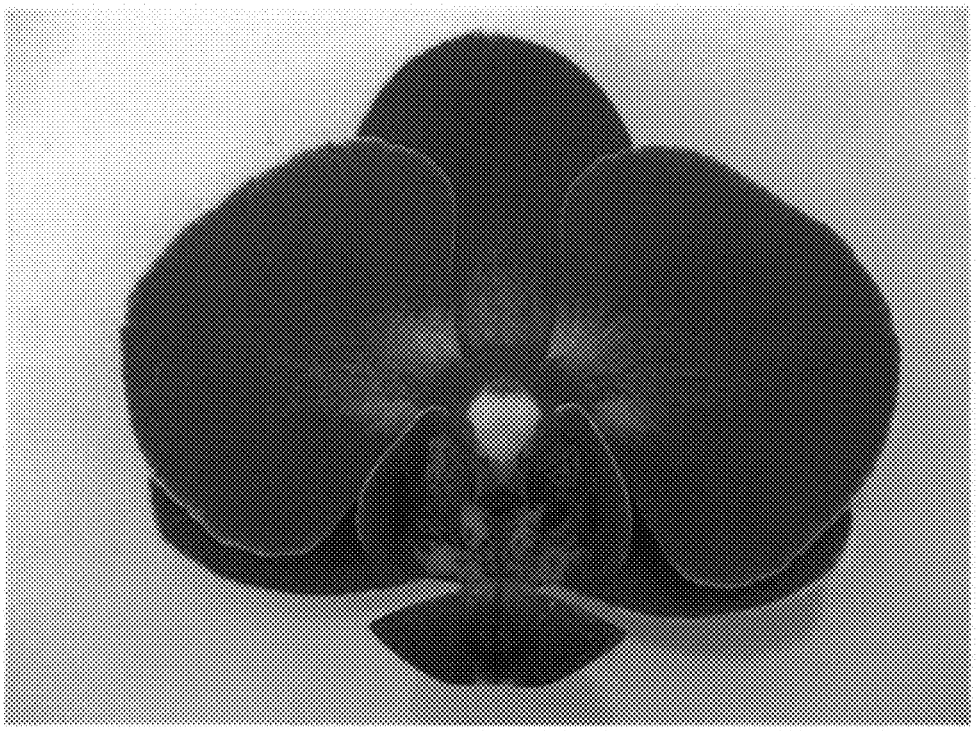
FIG. 2 shows a close-up of a flower of 'PHALDRAWEQ'.
Figure 3:
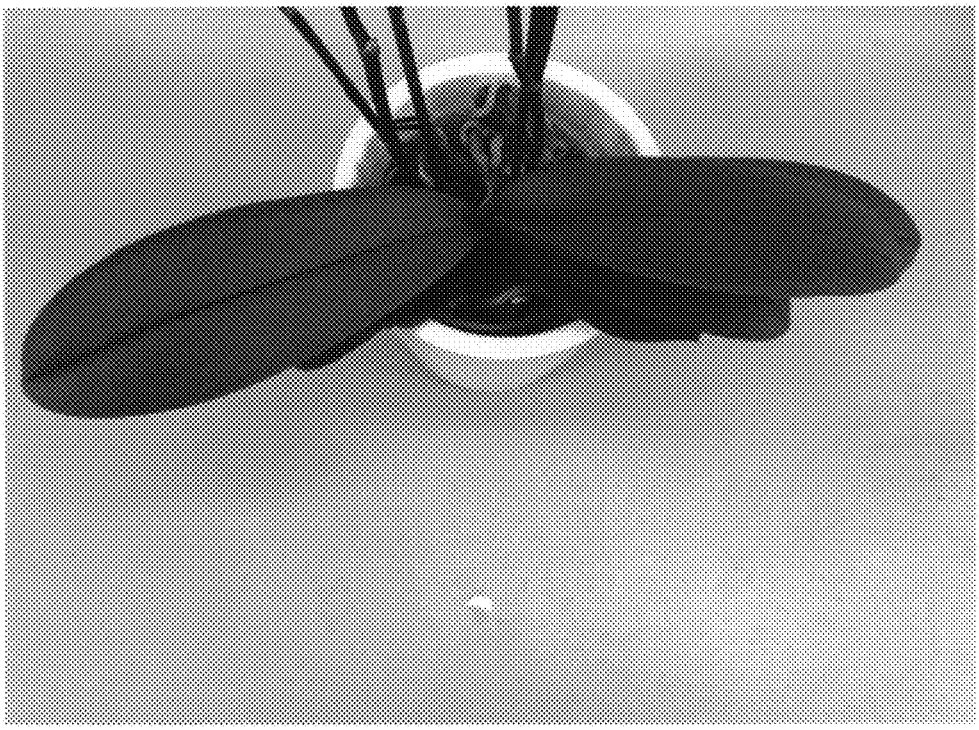
FIG. 3 shows a close-up of the leaves of 'PHALDRAWEQ'.

The following detailed description sets forth the distinctive characteristics of 'PHALDRAWEQ'. Plants of the new *Phalaenopsis* have not been observed under all possible environmental conditions. The phenotype may vary somewhat with variations in environment such as temperature, light intensity and day length, without, however, any variance in genotype. The chart used in the identification of colors described herein is The R.H.S. Colour Chart of The Royal Horticultural Society, London, England, 2015 edition, except where general color terms of ordinary significance are used. The color values were determined under 4000-6000 lux natural light in a greenhouse in Bleiswijk, The Netherlands. Observations and measurements were made in September 2016 on 50-week old plants which were planted from a nursery tray in 12 centimeter (diameter) pots and grown in a greenhouse between 27° C. to 29° C. for 30 weeks, continued by a cooling period of 8 weeks between 18° C. to 20° C. and 12 weeks in a greenhouse of 21° C.

DETAILED BOTANICAL DESCRIPTION

Classification:

*Family*.—Orchidaceae.

*Botanical*.—*Phalaenopsis* hybrid.

*Common name*.—Moth orchid.

*Variety name*.—'PHALDRAWEQ'.

Parentage:

*Female parent*.—*Phalaenopsis* cultivar 'unknown'.

*Male parent*.—*Phalaenopsis* cultivar 'unknown'.

Propagation:

*Type*.—Meristem tissue culture.

Roots:

*Root description*.—Greyed-green (RHS 191C/D) colored roots with branching lateral roots having diluting dark red (RHS 187A/B) colored root tips.

Plant:

*Commercial crop time to flowering*.—Approximately 48 to 50 weeks from a rooted cutting to finish in a 12 cm pot.

*Growth habit of peduncle*.—Standard, green leaves, raceme to panicle.

*Height* (*from soil level to top of inflorescence*).—Approximately 26.0 cm to 36.0 cm.

*Width* (*measured from leaf tips*).—About 30.0 cm to 35.0 cm.

*Vigor*.—Strong.

Leaves:

*Mature leaves*.—Quantity per plant: 7 to 10 leaves are produced before flowering. Length (fully expanded): 16.0 cm to 18.0 cm. Width: 6.0 cm to 7.0 cm. Shape: Oblong. Base shape: Moderately elongated. Apex: Unequal obtuse. Leaf blade angle with the petiole (measured from the horizontal position): Between 25 degrees and 40 degrees. Leaf margin: Entire. Color: Upper surface: RHS 147A. Lower surface: RHS 147B and 187A at the edge. Variegation: Absent. Texture: Rough. Thickness: 2.3 mm to 2.7 mm. Venation: Pattern: Parallel. Color of the midvein: Upper surface: RHS 147A. Lower surface: RHS 147B and 187A.

Peduncle:

*Quantity per plant*.—1 to 3.

*Number of flowers per peduncle*.—15 to 25.

*Length*.—32.0 cm to 37.0 cm.

*Diameter*.—4.6 mm to 4.9 mm.

*Strength*.—Strong.

*Aspect*.—Upright to slightly pendant.

*Texture*.—Smooth.

*Color*.—Brown (RHS 200A).

*Internode length*.—4.0 cm to 5.0 cm.

*Callosities*.—None.

Inflorescence description:

*Appearance*.—Upright to slightly pendant, panicle inflorescence with bilaterally symmetrical flowers that open in succession beginning with the lowermost flower.

*Inflorescence size*.—Height (from base to tip): 250.0 mm to 300.0 mm.

*Number of inflorescences per plant*.—1 to 3.

*Flowering time*.—First flowers can be expected 10 to 11 months after planting in a 12 cm (diameter) pot.

*Flower*.—Height: 45.0 mm to 50.0 mm. Diameter: 55.0 mm to 60.0 mm. Depth of lip: 16.0 mm to 18.0 mm.

*Flower longevity*.—On the plant: 10 to 14 weeks.

*Fragrance*.—Absent.

*Flower bud*.—Length: 18.0 mm to 20.0 mm. Width: 15.0 mm to 17.0 mm. Shape: Egg shaped. Color: Light green (RHS 145C/D) with a touch of diluted purple (RHS N77D).

*Petals*.—Arrangement: Open/free. Shape: Semi-circular. Apex: Rounded asymmetric. Margin: Entire. Length (from base to tip): 25.0 mm to 27.0 mm. Width: 29.0 mm to 31.0 mm. Position of broadest part of petal: Toward the apex. Color (when fully opened): Upper surface: Basic color: Purple (RHS N79C). Over color: Light purple (RHS N80D) at the center and edge. Lower surface: Basic color: Diluted purple (RHS N79). Over color: Light purple (RHS N78C) and towards the middle of the petal (RHS 76C).

*Dorsal sepal*.—Shape: Elliptic. Apex: Rounded symmetric. Margin: Entire. Length (from base to tip): 29.0 mm to 31.0 mm. Width: 22.0 mm to 24.0 mm. Color (when fully opened): Upper surface: Basic color: Purple (RHS N79C). Over color: Slightly light purple (RHS N80D) towards the center. Lower surface: Basic color: Light purple (RHS 76C). Over color: Diluted purple (RHS N79C) at the edge.

*Lateral sepals*.—Shape: Ovate. Apex: Obtuse asymmetric. Margin: Entire. Length (from base to tip): 26.0 mm to 28.0 mm. Width: 21.0 mm to 23.0 mm. Color (when fully opened): Upper surface: Basic color: Purple (RHS N79C). Over color: Slightly light green (RHS 145C) and red-purple (RHS 59A) towards the center. Lower surface: Basic color: Light purple (RHS 76C). Over color: Light green (RHS 145C) towards the center and diluted edge (RHS N79C).

*Labellum* (*lip*).—Whiskers: Present. Length of whiskers: 3.0 mm to 5.0 mm. Color of whiskers: Dark purple (RHS 187B) with white (RHS NN155C) tips. Pubescence on the lip: Absent.

*Lateral lobe*.—Shape: Weakly spatulate. Margin: Entire. Length (from base to tip): 15.0 mm to 17.0 mm. Width: 9.0 mm to 11.0 mm. Color: Dark red (RHS 187B) and slightly yellow (RHS 10B) at the base.

*Apical lobe*.—Shape: Circular. Margin: Entire. Length: 16.0 mm to 18.0 mm. Width: 13.0 mm to 15.0 mm. Color: Dark red (RHS 187B) and yellow (RHS 5B) at the base.

*Callus*.—Average size: Medium. Height: 5.0 mm to 6.0 mm. Length: 6.0 mm to 7.0 mm. Width: 3.0 mm to 4.0 mm. Color: Light yellow (RHS 5B) and spotted (RHS 59B).

*Reproductive organs*.—Column: Length: 7.0 mm to 9.0 mm. Diameter: 4.6 mm to 4.9 mm. Color: Purple (RHS N78A). Pollinia: Quantity: 2. Diameter: 0.8 mm to 1.0 mm. Color: Yellow-orange (RHS 23A). Ovary: Length: 12.0 mm to 14.0 mm. Diameter: 2.1 mm to 2.3 mm. Pedicel: Length: 32.0 mm to 34.0 mm. Diameter: 1.7 mm to 1.9 mm. Color: Green (RHS 147A) at the base; light purple (RHS N75B/C) towards the flower.

Disease, pest, and stress resistance: No specific resistance or susceptibility observed to pathogens and pests common to *Phalaenopsis*.

Fruit and seeds: Fruit and seed development has not been observed on plants of the new *Phalaenopsis*.

COMPARISON WITH PARENTAL AND COMMERCIAL VARIETIES

The female parent of 'PHALDRAWEQ' is unknown, so a meaningful comparison cannot be made.

The male parent of 'PHALDRAWEQ' is unknown, so a meaningful comparison cannot be made.

'PHALDRAWEQ' is most similar to the commercial *Phalaenopsis* plants named 'PHALDIMXAP' (U.S. Plant Pat. No. 25,294) and 'PHALBIQEQ' (unpatented). 'PHALDRAWEQ' differs from the commercial variety 'PHALDIMXAP' in that 'PHALDRAWEQ' has purple (RHS N79C) flowers, a dark red apical lobe with yellow at the base and a pedicel with green (RHS 147A) at the base and light purple (RHS N75B/C) towards the flower, whereas 'PHALDIMXAP' has purple (RHS 77A) flowers, an evenly colored dark purple apical lobe and a pecidel that is light green (RHS 146A and 146D) and light purple (RHS N80D). Additionally, 'PHALDRAWEQ' has longer whiskers than 'PHALDIMXAP'.

'PHALDRAWEQ' differs from the commercial variety 'PHALBIQEQ' in that 'PHALDRAWEQ' has purple flowers, a dark red apical lobe with yellow at the base, a pedicel with green at the base and light purple towards the flower, no pubescence on the callus and a rounded petal apex, whereas 'PHALBIQEQ' has violet flowers, a violet apical lobe with darker center, a light purple pedicel, pubescence on the callus and an obtuse petal apex. Additionally, 'PHALDRAWEQ' has larger flowers and longer whiskers than 'PHALBIQEQ'.

I claim:

1. A new and distinct variety of *Phalaenopsis* plant named 'PHALDRAWEQ', substantially as described and illustrated herein.

* * * * *